United States Patent [19]

Munro et al.

[11] Patent Number: 5,420,125
[45] Date of Patent: May 30, 1995

[54] NITROMETHYLENE COMPOUNDS

[75] Inventors: David Munro, Maidstone; Bipin Patel, Sittingbourne, both of England

[73] Assignee: Shell Research Limited, United Kingdom

[21] Appl. No.: 217,150

[22] Filed: Mar. 24, 1994

[30] Foreign Application Priority Data

Mar. 26, 1993 [EP] European Pat. Off. ............ 93302401

[51] Int. Cl.6 .................... C07D 279/06; A01N 43/86
[52] U.S. Cl. ................... 514/226.8; 544/54; 544/55
[58] Field of Search .................. 544/55, 54; 514/226.8

[56] References Cited
U.S. PATENT DOCUMENTS 3,993,648 11/1976 Powell ............................. 260/243

OTHER PUBLICATIONS

Chem. Abstracts, 89:101948h (1978).

*Primary Examiner*—John M. Ford

[57] ABSTRACT

Nitromethylene compounds of general formula

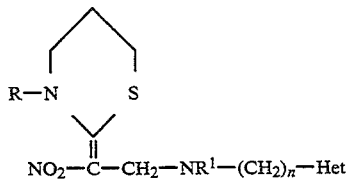

wherein R represents a hydrogen atom or an alkyl group, $R^1$ represents a hydrogen atom or an alkyl group, n is 0 or 1, and Het represents an optionally substituted 3-pyridyl, 4-pyridyl or 5-isoxazolyl group, processes for their preparation, and their use as insecticides, are described.

11 Claims, No Drawings

NITROMETHYLENE COMPOUNDS

This invention relates to nitromethylene compounds, to processes for their preparation and to the use of such compounds as pesticides.

U.S. Pat. No. 3,993,648 (Shell Oil Company) discloses nitromethylene compounds of general formula

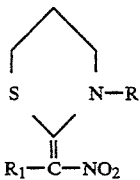

together with resonance hybrids, geometric isomers, and tautomers, as well as mixtures thereof, and salts, wherein R represents hydrogen, alkyl, alkenyl, alkoxyalkyl, cycloalkyl, cyanoalkyl, haloalkenyl, aralkyl or alkoxycarbonylvinyl and $R^1$ represents hydrogen or alkyl, alkenyl, alkynyl, haloalkyl, haloalkenyl, halo(hydroxy)alkyl, alkoxyalkyl, cyanoalkyl, hydroxyalkyl, alkoxycarbonylalkyl, alkylcarbonylalkyl, alkylthioalkyl, alkylsulfinylalkyl, aryl, aralkyl or arylthio optionally substituted on the ring by one or more of halogen, nitro, cyano, alkyl, aryl, alkoxy or aryloxy; halogen: aminomethyl, $—CH_2—NR^2R^3$, where $R^2$ is alkyl, hydroxyalkyl, alkoxyalkyl, cycloalkyl, alkenyl, aryl, haloaryl or aralkyl, and $R^3$ is hydrogen or one of the moieties represented by $R^2$;

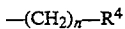

wherein n is zero, one or two, and $R^4$ is a heteromonocyclic moiety of from five to six carbon atoms in the ring, containing in the ring carbon atoms and one to two of oxygen (—O—) sulphur (—S—) and nitrogen (=N—, or —NH—) bonded to carbon in the ring, or is drawn, in the specification of U.S. Pat. No. 3,993,648, as

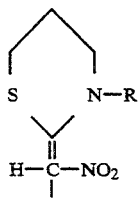

The compounds of U.S. Pat. No. 3,993,648 are said to exhibit useful insecticidal activity, being of particular interest for control of larval forms of insects, for example corn earworm. Some activity of certain compounds against whiteflies and houseflies is also mentioned.

It is believed that the most active compound of those disclosed in U.S. Pat. No. 3,993,648 is tetrahydro-2-(nitromethylene)-2H-1,3 thiazine ($R=R^1=H$). However, no compounds of U.S. Pat. No. 3,993,648 advanced to commercialisation.

This invention is based on the discovery of novel nitromethylene thiazine compounds which exhibit pesticidal activity. Certain compounds of the present invention have been found to exhibit insecticidal activity which compares well with that of the compound of U.S. Pat. No. 3,993,648, mentioned above, which is believed to be the most active compound thereof.

According to the present invention, there is provided nitromethylene thiazine compounds of general formula

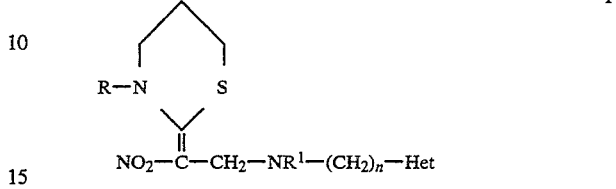

wherein R represents a hydrogen atom or an alkyl group, $R^1$ represents a hydrogen atom or an alkyl group, n is 0 or 1, and Het represents an optionally substituted 3-pyridyl, 4-pyridyl or 5-isoxazolyl group.

Unless otherwise stated in this specification, an alkyl group may be linear or branched and suitably contains up to 10, preferably up to 6, and most preferably up to 4, carbon atoms, preferred examples being methyl and ethyl.

Unless otherwise stated in this specification, when a group is designated as being optionally substituted, the substituent groups which are optionally present may be any of those customarily employed in the development of pesticidal compounds, and/or the modification of such compounds to influence their structure/activity, persistence, penetration or other property.

Preferably R represents a hydrogen atom.

Preferably $R^1$ represents a hydrogen atom or, preferably, a methyl group.

Preferably n is 1.

Optional substituents of the group Het may include halogen atoms, for example fluorine, chlorine, bromine and iodine atoms, and nitro, cyano, alkoxy, hydroxy, (alkyl)amino, alkyl and haloalkyl (especially $CF_3$) groups. Preferred optional substituents include halogen atoms, especially chlorine, and $C_{1-4}$ alkyl groups, especially methyl. The most favourable substituent appears to be chlorine. There may suitably be one or two substituents.

A preferred 4-pyridyl group is unsubstituted.

A preferred 3-pyridyl group has a substituent at the 6-position (relative to the N atom) and optionally a further substituent at the 5-position (relative to the N atom).

A preferred 5-isoxazolyl group has a substituent at the 3-position (relative to the O atom).

Three particularly preferred groups Het are 3-chloro-5-isoxazolyl, 6-chloro-3-pyridyl and 5,6-dichloro-3-pyridyl.

Included in the scope of the present invention are geometric isomers, tautomers and salts, including salts with metal ions, and acid addition salts.

The invention further provides a process for the preparation of a compound of general formula I as defined above which comprises treating a compound of general formula

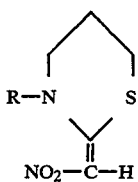

II with formaldehyde and with a compound of general formula

HNR$^1$—(CH$_2$)$_n$—Het      III; or treating a compound of general formula

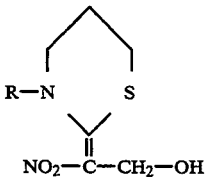

IV with a compound of general formula

HNR$^1$—(CH$_2$)$_n$—Het      III wherein in each of compounds of general formula II, III and IV, R, R$^1$, n and Het are as described above: and optionally alkylating a resultant compound of general formula I in which R represents a hydrogen atom, to prepare a compound of general formula I in which R represents an alkyl group.

Preferably, the preparation of the compound of general formula I starting from the compound of general formula II involves mixing the compound of general formula II and formaldehyde together in the presence of an inert solvent. Suitable solvents include alcohols, for example, methanol or ethanol. Said compound of general formula III may then be added. The reaction is preferably carried out at a temperature in the range −20° to 60° C., preferably 0° to 20° C. suitably with stirring. Preferably the reaction is carried out with cooling, the reaction temperature being within the range 5° to 15° C. After subsequent removal of the solvent, the desired product may be isolated by standard procedures.

Preferably, the preparation of the compound of general formula I starting from the compound of general formula IV involves reacting compounds of general formula IV and III together in an inert solvent, for example, an alcohol, for example methanol or ethanol. The reaction is preferably carried out at a temperature within the range −20° to 60° C. preferably 0° C. to 20° C. suitably with stirring, Preferably the reaction is carried out with cooling, the reaction temperature being within the range 5° to 15° C. After removal of the solvent, the product may be isolated by standard procedures.

To prepare a compound of general formula I in which R represents an alkyl group, a compound of general formula I in which R represents a hydrogen atom may be alkylated, or an intermediate compound may be alkylated. Standard alkylation methods may be used. Reference may here be made to the alkylation methods described in U.S. Pat. No. 3,993,648.

Compounds of general formula It may be prepared as described in U.S. Pat. No. 3,993,648. Compounds of general formula IV may be prepared by reacting a compound of general formula II with formaldehyde as described above. Compounds of general formula III are either known materials or may be prepared by standard procedures, for example starting with the appropriately substituted 3-nitropyridine or 3-hydroxymethylpyridine, or corresponding isoxazole.

The compounds of general formula I exhibit pesticidal, particularly insecticidal, activity. Accordingly, the invention also provides a pesticidal composition comprising a carrier and, as active ingredient, a compound of general formula I. The invention further provides a method of combating pests at a locus, which comprises treating the locus with a pesticidal compound or composition according to the invention, and specifically provides the use as an insecticide of a compound of general formula I.

Particularly interesting activity has been observed against larval pests, especially of lepidoptera species. The target pests may be larval "caterpillar" or "worm" forms of insects of the genus Heliothis, such as *H. zea* (corn earworm), cotton bollworm, tomato fruitworm, and *H. virescens* (tobacco budworm): the genus Agrotis, such as *A. ipsilon* (black cutworm); the genus Trichoplusia, such as *T. ni* (cabbage looper); and, especially, the genus Spodoptera, such as *S. littoralis* (Egyptian cotton leafworm). A preferred aspect of the present invention therefore relates to the pesticidal treatment of such pests.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to for a liquid, and any of the carriers normally used in formulating pesticidal compositions may be used. Preferably compositions according to the invention contain 0.5 to 95% by weight of active ingredient.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montomorilionites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers: solid polychlorophenols; bitumen; waxes; and solid fertilisers, for example superphosphates.

Suitable liquid carriers include water: alcohols, for example isopropanol and glycols: ketones, for example acetone, methyl ethyl ketone, methyl isobutyl ketone and cyclohexanone; ethers; aromatic or araliphatic hydrocarbons, for example benzene, toluene and xylene: petroleum fractions, for example kerosine and light mineral oils: chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus, preferably at least one carrier in a composition according to the invention is a surface-active agent. For example the composition may contain at least two carriers, at least one of which is a surface-active agent.

A surface-active agent may be an emulsifying agent, a dispersing agent or a wetting agent: it may be nonionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide: fatty acid esters of glycerol sorbitan, sucrose or pentaerythritol: condensates of these with ethylene oxide and/or propylene oxide: condensation products of fatty alcohol or alkyl phenols, for example p-octylphenyl or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3–10% w of a dispersing agent and, where necessary, 0–10% w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing ½–10% w of active ingredient. Granules are usually prepared to have a size between 10 and 100 BS mesh (1.676–0.152 mm), and may be manufactured by agglomeration or impregnation techniques. Generally, granules will contain ½–75% w active ingredient and 0–10% w of additives such as stabilisers, surfactants, slow release modifiers and binding agents. The so-called "dry flowable powders" consist or relatively small granules having a relatively higher concentration or active ingredient. Emulsifiable concentrates usually contain, in addition to a solvent and, when necessary, co-solvent, 10–50% w/v active ingredient, 2–20% w/v emulsifiers and 0–20% w/v or other additives such as stabilisers, penetrants and corrosion inhibitors. Suspension concentrates are usually compounded so as to obtain a stable, non-sedimenting flowable product and usually contain 10–75% w active ingredient, 0.5–15% w of dispersing agents, 0.1–10% w of suspending agents such as protective colloids and thixotropic agents, 0–10% w or other additives such as defoamers, corrosion inhibitors, stabilisers, penetrants and stickers, and water or an organic liquid in which the active ingredient is substantially insoluble: certain organic solids or inorganic salts may be present dissolved in the formulation to assist in preventing sedimentation or as antifreeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick "mayonnaise"-like consistency.

Compositions in accordance with the invention may also contain other ingredients, for example other compounds possessing pesticidal, herbicidal, or fungicidal properties. The compounds of the invention may be found to be especially useful when applied in admixture with other insecticides and/or acaricides, e.g. organophosphates, pyrethroids, ureas and organotin compounds, for example the commercial products fenvalerate, permethrin, cypermethrin, deltamethrin, alphacypermethrin, fenbutatin oxide, flufenoxuron diflubenzuron and trefluron.

The invention will be further understood from the following illustrative examples.

Example 1

Preparation of N-methyl,N-(6-chloro-3-pyridylmethyl)-2-nitro-2-(tetrahydro-2H-1,3-thiazine-2-ylidene)ethanamine

[n=1, R=H,R$^1$=CH$_3$, Het=6-chloro-3-pyridyl]

A solution of 4.4 g of N-methyl,N-(6-chloro-3-pyridylmethylamine (prepared by converting the corresponding pyridyl methanol to the chloromethyl derivative, then reacting with methylamine) in ethanol (5 ml) was added to a cooled (5° C.) mixture of tetrahydro-2-(nitromethylene)-2H-3-thiazine (4 g), also in ethanol (20 ml). At 8°–12° C., 2.8 g of a 37% w aqueous solution of formaldehyde was added dropwise. After stirring for 40 minutes at 8°–12° C. the reaction mixture temperature was permitted to rise to ambient temperature and stirring was stopped. A precipitate deposited. This was filtered and recrystallised from ethanol, yielding 5.6 g of the title compound. mp 102° C.

|  | Analysis | | |
| --- | --- | --- | --- |
|  | % C | % H | % N |
| Calc. | 47.5 | 5.2 | 17.0 |
| Found | 47.5 | 5.2 | 16.8 |

Examples 2 to 8

Further compounds as noted in Table 1 were prepared by processes analogous to the process of Example 1. Characterising data for the compounds of Examples 2 to 6 is noted in Table 1.

TABLE 1

| Example No. | R | R$^1$ | n | Het | m.p. (°C.) | Analysis CHN wt % Calculated Found | | |
| --- | --- | --- | --- | --- | --- | --- | --- | --- |
| 2 | H | CH$_3$ | 1 | 5,6-dichloro-3-pyridyl | 115 | 43.0 | 4.4 | 15.4 |
|  |  |  |  |  |  | 42.3 | 4.3 | 15.3 |
| 3 | H | CH$_3$ | 1 | 3-methyl-5-isoxazolyl | 104 | 48.3 | 6.1 | 18.8 |
|  |  |  |  |  |  | 47.7 | 6.0 | 18.2 |
| 4 | H | CH$_3$ | 1 | 3-chloro-5-isoxazolyl | 102 | 41.4 | 4.7 | 17.6 |
|  |  |  |  |  |  | 41.5 | 4.8 | 17.7 |
| 5 | H | CH$_3$ | 1 | 4-pyridyl | 138 | 53.1 | 6.1 | 19.0 |
|  |  |  |  |  |  | 53.0 | 6.3 | 19.2 |
| 6 | H | H | 0 | 6-chloro-3-pyridyl | 165 | 46.1 | 4.1 | 17.7 |
|  |  |  |  |  |  | 45.8 | 4.5 | 18.4 |
| 7 | H | C$_2$H$_5$ | 1 | 6-chloro-3-pyridyl |  |  |  |  |
| 8 | H | n-C$_3$H$_7$ | 1 | 6-chloro-3- |  |  |  |  |

TABLE 1-continued

| Example No. | R | R¹ | n | Het | m.p. (°C.) | Analysis CHN wt % Calculated Found |
|---|---|---|---|---|---|---|
| | | | | pyridyl | | |

EXAMPLE 9

Insecticidal Activity

Insecticidal activity of compounds of the invention was assessed against various of the following pests:
  *Spodoptera littoralis* (Egyptian cotton leafworm)
  *Aedes aegypti* (yellow fever mosquito)
  *Musca domestica* (housefly)
  *Acyrthosiphon pisum* (pea aphid)
  *Megoura viciae* (vetch aphid)
  *Trialeurodes vaporariorum* (greenhouse whitefly)
  *Nephotettix cincticeps* (green leaf hopper)

The test methods employed for each species appear below. In each test, unless otherwise stated, solutions or suspensions of test compound were made up over a range of concentrations in water (initially 0. 1% w) containing 10% w acetone and 0.025% w "TRITON X-100" (trade mark) surface active agent (the condensation product of ethylene oxide with an alkyl phenol). These solutions were sprayed at a rate equivalent to 340 liters per hectare ($3.4 \times 10^{-5} m^3/m^2$) onto Petri dishes containing either test species per se or diet onto which test species were subsequently introduced, as indicated. In some assays leaf discs infested with test species were sprayed whilst other assays involved the spraying of plants which were infested subsequently with test species after the spray solution had dried. The tests were all conducted under normal insectary conditions (23° C.±2° C., fluctuating humidity and light). Mortality assessments were made as indicated below, in terms of percentage mortality figures. In each test a $LC_{50}$ (the dosage of active material required to kill half of the test species) for the compound was calculated from the mortality figures and compared with the corresponding $LC_{50}$ for a standard insecticide, ethyl parathion, in the same test. The results are expressed as toxicity indices thus:

$$\text{toxicity index} \frac{LC_{50} \text{ (parathion)}}{LC_{50} \text{ (test compound)}} \times 100$$

(i) *Spodoptera littoralis* (1 day and 7 day)(Sl 1D; Sl 7D)

Test solutions were sprayed as indicated above onto Petri dishes containing a nutritious diet for Egyptian cotton leafworm larvae. When the spray deposit had dried, each dish was infested with ten 2nd instar larvae. Mortality assessments were made 1 and 7 days after spraying.

(ii) *Spodoptera littoralis* (foliar)(Sl 1Fol)

Test solutions were sprayed as described above onto Petri dishes containing 9 cm discs of Chinese cabbage leaves on filter papers. After drying, each dish was infested with ten 2nd instar larvae. Mortality assessments were made 24 hours after infestation.

(iii) *Spodoptera littoralis* (ovicidal)(Sl OA)

Test solutions were sprayed as described above onto Petri dishes containing filter papers on which were approximately 50 24 hour old eggs. After 6 days the numbers of hatched and unhatched eggs were counted and percentage mortality calculated.

(iv) *Aedes aegypti* (Aa)

Early 4th instar larvae were used. Test solutions were made up to 0.5 ppm of test compound (and progressive half-dilutions) in water containing 0.04% w "TRITON X-100" (trade mark); acetone was initially present to aid solution, but was allowed to evaporate off before introduction of larvae.

Ten early 4th instar larvae were placed in 100 ml of test solution held at 28° C., and after 48 hours, larval mortality was recorded. The final mortality was assessed by counting the number of emerged adult mosquitoes after one week.

(v) *Musca domestica* (Md)

Batches of ten 2 to 3 day old milk-fed adult female houseflies, anaesthetised using carbon dioxide, were placed on filter papers inside Petri dishes. The dishes were sprayed with the test solutions as described above. The flies were retained in the Petri dishes and were fed with a dilute milk solution which was dripped down the side of the Petri dish and absorbed by the filter paper. Mortality was assessed after 24 hours.

(vi) *Acyrthosiphon pisum* (Ap)

Tests were carried out on young adult pea aphids. Whole pea plants 6 days after germination were placed on filter papers in Petri dishes. Ten aphids were transferred to each pea plant and left for 30 minutes to allow the aphids to settle and start to feed. The dishes were then sprayed with the test solutions as described above and lids were placed on the Petri dishes. Mortality was assessed after 24 hours.

(vii) *Megoura viciae* (Mv)

Tests were carried out on adult-Vetch aphids. Pairs of broad bean leaves on filter paper in Petri dishes were sprayed side by side with uncounted quantities of aphids in small gauze-covered containers. After passing through the spray ten aphids were tipped onto the leaves and lids were placed on the Petri dishes. Mortality was assessed after 24 hours.

(viii) *Trialeurodes vaporariorum* (Tv)

French bean plants (*Phaseolus vulgaris*) with two fully expanded leaves were placed in a breeding culture of *T. vaporariorum*, also on French bean plants, which were then disturbed to ensure resettlement on the introduced plants. During the subsequent 24 hour period, eggs were deposited and kept at 27° C. with 14 hours photoperiod. All adult whiteflies were then carefully removed, leaving egg samples of a known age. After eight days the majority of eggs had hatched. Leaf discs containing the newly hatched nymphs were then cut from the leaves and transferred to moist filter paper. The discs were examined under a low-powered microscope to determine the exact number of 1st instar nymphs per disc and to remove any unhatched eggs. On average, 70–100 nymphs were found per disc.

The discs were transferred into Petri dishes and sprayed with test solutions as described above. After 6 days percentage mortalities were assessed.

(ix) *Nephotettix cincticeps* (Nc)

Tests were carried out on young adult female green leaf hoppers. Plant pots, each containing five rice seedlings 10 to 15 cm tall arranged across the centre of the pot, were sprayed with test solutions as described above (but initial test concentration 0.05% of test compound). Spraying was on both sides of the plants with the pots horizontal. One hour after spraying, each pot was filled to the brim with fine silver sand, an open-ended glass jar was placed over each pot and each pot was infested with ten hoppers. A paper tissue was placed over the open end of each glass jar to retain the hoppers. The pots were irrigated from underneath, maintained at a temperature of 27° C.±2° C. and subjected to white fluorescent light under a regime of 18 hours light followed by 6 hours darkness. Mortality assessments were made 48 hours after infestation.

EXAMPLE 10

Acaricidal Activity (ovicide)(Tu OA)

Acaricidal activity of the compounds of Examples 1 to 6 was assessed, employing eggs of the glasshouse red spider mite, *Tetranychus urticae* (T. u.), less than 24 hours old, by the following procedure.

2 cm diameter leaf discs cut from the leaves of French bean plants were placed on filter paper, kept moist by a cotton wool wick dipped into water.

On the day before spraying, each leaf disc was infested with 10 female adult mites. On the day of the test, the adults were removed, leaving the eggs laid overnight on the discs. The leaf discs were then sprayed with solutions of test compound made up as in Example 7 above, at a rate equivalent to 340 liters per hectare $(3.4 \times 10^{-5} \, m^3/m^2)$.

Throughout the test, the eggs were held under normal insectary conditions (23° C.±2° C., fluctuating humidity and 16 hours days length). After 7–10 days, the numbers of hatched nymphs and unhatched eggs were assessed and the percentage mortality calculated. The $LC_{50}$ (the dosage of active material required to kill half of the test species) for the compound was calculated from the mortality figure and compared with the corresponding $LC_{50}$ for a standard insecticide, chlorfenson, in the same test. The result is expressed as toxicity index thus:

$$\text{toxicity index} \, \frac{LC_{50} \, (\text{chlorfenson})}{LC_{50} \, (\text{test compound})} \times 100$$

Results of the assessments described in Examples 9 and 10 for each of the compounds of Examples 1 to 6 are provided in Table 2. Also shown are the results of testing the comparison compound tetrahydro-2-(nitromethylene)-2H-1,3-thiazine, believed to be the most active compound disclosed in U.S. Pat. No. 3,993,648 (called Example C1). In Table 2 a blank square indicates that testing was not carried out. The letters B and C indicate that the first test carried out at the initial test concentration of 0.1% wt (1000 ppm) gave a mortality assessment of 40–69% and 0–39%, respectively. When that initial test yielded a mortality assessment of 70–100%, a rating of A would be given. Usually further testing to yield toxicity indices as described above was carried out. Toxicity indices are stated, where available.

TABLE 2

| Compound of Example | S1 1D | S1 7D | S1 Fol | S1 OA | Aa | Md | Ap | Mv | Tv | Nc | Tu OA |
|---|---|---|---|---|---|---|---|---|---|---|---|
| 1 | C | 18 | 150 | 84 | C | 4 | C | 0 | C | 32 | C |
| 2 | C | 23 | 180 | | 7 | 4 | 4 | 0 | | B | <22 |
| 3 | <17 | 25 | 91 | C | <4 | 4 | C | 0 | C | 24 | C |
| 4 | B | B | 140 | 98 | C | 3 | C | 0 | C | 36 | C |
| 5 | 24 | 14 | 74 | | C | 6 | 1 | 0 | | 120 | |
| 6 | B | <14 | <25 | C | | 6 | | 0 | C | C | C |
| 7 | | | | | | | | | | | |
| 8 | | | | | | | | | | | |
| C1 | C | 35 | 87 | 55 | A | 36 | 5 | 0 | 140 | A | C |

We claim:

1. A compound of the formula:

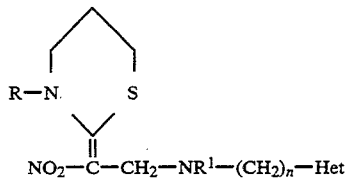

$$NO_2-C-CH_2-NR^1-(CH_2)_n-Het$$

wherein R represents a hydrogen atom or a linear or branched $C_{1-10}$ alkyl group, $R^1$ represents a hydrogen atom or a linear or branched $C_{1-10}$ alkyl group, n is 0 or 1, and Het represents an optionally substituted 3-pyridyl, 4-pyridyl or 5-isoxazolyl group, said optional Het substituents being selected from the group consisting of halogen, nitro, cyano, alkoxy, hydroxy, (alkyl)amino, alkyl and haloalkyl.

2. A compound as claimed in claim 1, wherein $R^1$ represents a hydrogen atom or a methyl group.

3. A compound as claimed in claim 1, wherein R represents a hydrogen atom.

4. A compound as claimed in claim 1, wherein n is 1.

5. A compound as claimed in claim 1, wherein Het represents a 3-pyridyl, 4-pyridyl or 5-isoxazolyl group, each being optionally substituted by one or two substituents selected from halogen and $C_{1-4}$ alkyl groups.

6. A compound as claimed in claim 5, wherein Het represents a 3-chloro-5-isoxazolyl group, or a 6-chloro-3-pyridyl group, or a 5,6-dichloro-3-pyridyl group.

7. A process for the preparation of a compound of formula I as claimed in claim 1 which comprises treating a compound of formula

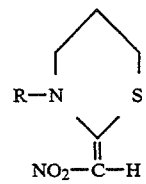

$$NO_2-C-H$$

with formaldehyde and with a compound of formula $$HNR^1-(CH_2)_n-HET \qquad\qquad III;\text{ or}$$

treating a compound of formula

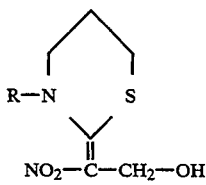

with a compound of general formula

HNR$^1$-(CH$_2$)$_n$—Het     III wherein in each of compounds of formulae II, III and IV, R, R$^1$, n and Het are as defined in claim 1; and optionally alkylating a resultant compound of formula I in which R represents a hydrogen atom, to prepare a compound of formula I in which R represents a linear or branched C$_{1-10}$ alkyl group.

8. An insecticidal or acaricidal composition comprising a carrier and, as an active ingredient, an effective amount of a compound of formula I as claimed in claim 1.

9. A method of combating insects or acarids at a locus, which comprises treating the locus with an effective amount of a compound as claimed in claim 1.

10. A method as claimed in claim 9, wherein the compound or composition is employed to combat larvae of lepidoptera species.

11. A method of combating insects or acarids at a locus, which comprises treating the locus with an effective amount of a composition as claimed in claim 8.

* * * * *